(12) United States Patent
Furukawa et al.

(10) Patent No.: US 7,189,548 B2
(45) Date of Patent: Mar. 13, 2007

(54) MODIFIED SARCOSINE OXIDASES, GENES AND RECOMBINANT DNAS THEREOF, AND METHODS FOR PREPARING THE SAME

(75) Inventors: Keisuke Furukawa, Chiba (JP); Naoki Kajiyama, Chiba (JP)

(73) Assignee: Kikkoman Corporation, Noda (JP)

( * ) Notice: Subject to any disclaimer, the term of this patent is extended or adjusted under 35 U.S.C. 154(b) by 128 days.

(21) Appl. No.: 10/829,427

(22) Filed: Apr. 22, 2004

(65) Prior Publication Data
US 2005/0026265 A1    Feb. 3, 2005

(30) Foreign Application Priority Data
Apr. 25, 2003  (JP) ............................. 2003-121533
Nov. 27, 2003  (JP) ............................. 2003-396807
Apr. 12, 2004  (JP) ............................. 2004-116345

(51) Int. Cl.
C12N 9/04   (2006.01)
C12N 1/20   (2006.01)
C07H 21/24  (2006.01)

(52) U.S. Cl. ................ 435/189; 536/23.2; 435/252.3; 435/252.31

(58) Field of Classification Search ............... 435/189, 435/252.3, 252.31; 536/23.2
See application file for complete search history.

(56) References Cited
OTHER PUBLICATIONS

Nishiya Y. et al. Analysis of Interaction between the Arthrobacter Sarcosine Oxidase and the Coenzyme Flavin Adenine Dinucleotide by Site-Directed Mutagenesis, Applied and Environmental Microbiology, 1996, 62 (7), 2405-2410.*

Nishiya Y. A Mutnt Sarcosine Oxidase in Which Activity Depends on Flavin Adenine Dinuclotide, Protein Expression and Purifiction, 2000, 20, 95-97.*

* cited by examiner

*Primary Examiner*—Rebecca E. Prouty
*Assistant Examiner*—Malgorzata A. Walicka
(74) *Attorney, Agent, or Firm*—Oblon, Spivak, McClelland, Maier & Neustadt, P.C.

(57) ABSTRACT

(1) A modified sarcosine oxidase with improved stability in the acidic range compared to a wild-type sarcosine oxidase.
(2) A sarcosine oxidase gene encoding a modified sarcosine oxidase of the following (a), (b), or (c):

(a) protein composed of the amino acid sequence represented by SEQ ID NO: 1
(b) protein composed of an amino acid sequence wherein one or some amino acid(s) are deleted, substituted, or added from the amino acid sequence represented by SEQ ID NO: 1, and which has sarcosine oxidase activity
(c) protein composed of an amino acid sequence which shows 80% or more homology to the amino acid sequence represented by SEQ ID NO: 1, and which has sarcosine oxidase activity According to the present invention, sarcosine oxidases, in particular sarcosine oxidases which show optimal pH and high activity in the slightly acidic range and have improved stability can be prepared efficiently, thus making the invention industrially useful.

2 Claims, 5 Drawing Sheets

SEQUENCE LISTING

<160> NUMBER OF SEQ ID NOS: 4

<210> SEQ ID NO 1
<211> LENGTH: 387
<212> TYPE: PRT
<213> ORGANISM: Artificial Sequence
<220> FEATURE:
<223> OTHER INFORMATION: Synthetic Peptide

<400> SEQUENCE: 1

```
Met Ser Thr His Phe Asp Val Ile Val Val Gly Ala Gly Ser Met Gly
1               5                   10                  15

Met Ala Ala Gly Tyr Tyr Leu Ala Lys Gln Gly Val Lys Thr Leu Leu
            20                  25                  30

Val Asp Ala Phe Asp Pro Pro His Thr Glu Gly Ser His His Gly Asp
        35                  40                  45

Thr Arg Ile Ile Arg His Ala Tyr Gly Glu Gly Arg Lys Tyr Val Pro
    50                  55                  60

Phe Ala Leu Arg Ala Gln Glu Leu Trp Tyr Glu Leu Glu Asn Glu Thr
65                  70                  75                  80

His Asn Lys Ile Phe Thr Lys Thr Gly Val Leu Val Phe Gly Pro Lys
                85                  90                  95

Gly Glu Ser Asp Phe Val Ala Glu Thr Met Glu Ala Ala Glu His
            100                 105                 110

Ser Leu Thr Val Asp Leu Leu Glu Gly Asp Glu Ile Asn Thr Arg Trp
            115                 120                 125

Pro Gly Ile Thr Val Pro Glu Asn Tyr Asn Ala Ile Phe Glu Pro Asn
        130                 135                 140

Ser Gly Val Leu Phe Ser Glu Asn Cys Ile Arg Ser Tyr Arg Glu Leu
145                 150                 155                 160

Ala Val Ala Lys Gly Ala Lys Ile Leu Thr Tyr Thr Arg Val Glu Asp
                165                 170                 175

Phe Glu Val Ser Gln Asp Gln Val Lys Ile Gln Thr Ala Asn Gly Ser
            180                 185                 190

Tyr Thr Ala Asp Lys Leu Ile Val Ser Met Gly Ala Trp Asn Ser Lys
        195                 200                 205

Leu Leu Ser Lys Leu Asn Leu Asp Ile Pro Leu Gln Pro Tyr Arg Gln
210                 215                 220

Val Val Gly Phe Phe Asp Ser Asn Glu Ala Lys Tyr Ser Asn Asp Val
225                 230                 235                 240

Gly Tyr Pro Ala Phe Met Val Glu Val Pro Lys Gly Ile Tyr Tyr Gly
                245                 250                 255

Phe Pro Ser Phe Gly Gly Cys Gly Leu Lys Ile Gly Tyr His Thr Tyr
            260                 265                 270

Gly Gln Gln Ile Asp Pro Asp Thr Ile Asn Arg Glu Phe Gly Ala Tyr
        275                 280                 285

Gln Glu Asp Glu Ser Asn Leu Arg Asp Phe Leu Glu Lys Tyr Met Pro
    290                 295                 300

Glu Ala Asn Gly Glu Leu Lys Arg Gly Ala Val Cys Met Tyr Thr Lys
305                 310                 315                 320

Thr Pro Asp His His Phe Val Ile Asp Thr His Pro Glu His Ser Asn
                325                 330                 335

Val Phe Val Ala Ala Gly Phe Ser Gly His Gly Phe Lys Phe Ser Ser
            340                 345                 350

Val Val Gly Glu Val Leu Ser Gln Leu Ala Thr Thr Gly Lys Thr Glu
        355                 360                 365

His Asp Ile Ser Ile Phe Ser Ile Asn Arg Pro Ala Leu Lys Gln Lys
    370                 375                 380

Thr Thr Ile
385
```

<210> SEQ ID NO 2
<211> LENGTH: 1164
<212> TYPE: DNA
<213> ORGANISM: Artificial Sequence
<220> FEATURE:
<223> OTHER INFORMATION: Synthetic DNA

<400> SEQUENCE: 2

```
atgagtacac attttgatgt gattgttgtt ggagcaggat caatgggaat ggctgcaggg      60
tactatttag caaaacaagg agtcaaaaca ttattggtgg atgcattcga tccgccgcat     120
acagaaggaa gccatcacgg tgatactcgc attatccgcc atgcttacgg tgaaggaaga     180
gaatatgttc catttgcact aagagcacaa gaattatggt atgaacttga aaatgaaaca     240
cacaataaga tttttacaaa acaggcgtt ctagtttttg gtccgaaagg tgaatccgat      300
ttcgttgccg aaacaatgga ggcagctgca gaacattcat tgatcgtgga tttacttgag    360
ggtgatgaaa tcaatacgcg ctggcccggc ataacggttc ctgaaaacta taatgcaatt    420
tttgaaccaa attcaggcgt attgttcagt gagaattgta ttcgttcata ccgtgagctg    480
gctgtagcaa aaggagcaaa aattttaaca tatactcgtg ttgaggattt tgaagtttct    540
caagaccaag ttaaaatcca aacggcaaat ggatcgtaca cagctgataa attaatcgta    600
agtatgggtg cttggaatag taaactactt tctaaattaa atcttgacat cccattacag    660
ccataccgcc aagttgtagg attttttgat tctaatgaag caaagtacag caatgatgtg    720
gattatccag cattcatggt agaagtacca aaaggtattt attacggatt cccaagcttc    780
ggtggctgcg gtttgaaaat agggtatcat acgtatggtc aacaaatcga ccctgatacg    840
attaaccgtg aatttggtgc ttatcaagag gatgaaagta atcttcgcga tttcttggaa    900
aaatatatgc agaagcaaa tggcgagtta aaacgaggcg cagcttgtat gtacacgaaa    960
acaccagatg aacatttcgt gattgatact catccagaac attccaatgt tttcgtagca   1020
gctggttcct ctggacacgg ctttaaattt tcaagtgtag tcggtgaagt gttaagtcaa   1080
ttagcgacaa caggtaaaac agaacatgat atttcaattt tctcaataaa tcgtcctgct   1140
ttaaaacaga aacaacgat ttaa                                            1164
```

<210> SEQ ID NO 3
<211> LENGTH: 22
<212> TYPE: DNA
<213> ORGANISM: Artificial Sequence
<220> FEATURE:
<223> OTHER INFORMATION: Synthetic DNA

<400> SEQUENCE: 3

```
gtaccggatc cgctagcttt ac                                               22
```

<210> SEQ ID NO 4
<211> LENGTH: 21
<212> TYPE: DNA
<213> ORGANISM: Artificial Sequence
<220> FEATURE:
<223> OTHER INFORMATION: Synthetic DNA

<400> SEQUENCE: 4

```
cgacggccag agatctacta g                                                21
```

MODIFIED SARCOSINE OXIDASES, GENES AND RECOMBINANT DNAS THEREOF, AND METHODS FOR PREPARING THE SAME

BACKGROUND OF THE INVENTION

1. Field of the Invention

The present invention relates to modified sarcosine oxidases, genes and recombinant DNAs thereof, and methods for preparing the same.

2. Background Art

Sarcosine oxidases are enzymes with a catalytic activity to hydrolyze sarcosines to produce glycine and formaldehyde, which can be used to measure the amount of creatinine in human serum or urine, or can be utilized as diagnostic agents for various diseases such as renal disease.

Sarcosine oxidases are previously known to be produced by bacterial strains such as *Corynebacterium* genus (see J. Biochem., 89,599 (1981)), *Bacillus* genus (see JP Patent Publication (Unexamined Application) No. 54-52789), *Cylindrocarbons* genus (see JP Patent Publication (Unexamined Application) No. 56-92790), *Pseudomonas* genus (see JP Patent Publication (Unexamined Application) No. 60-43379), *Arthrobacters* genus (see JP Patent Publication (Unexamined Application) No. 2-265478). However, in typical creatine quantitative reactions in slightly alkaline range (pH 7.5–8.0), bilirubin affects the measurement value, thus causing a difficulty upon measuring. Until now, genetically modified enzymes having optimal pH in the slightly acidic range, which are produced by modifying sarcosine oxidase genes from *Bacillus* genus, aiming for measuring in the slightly acidic range where effects of bilirubin are less, are also known (see JP Patent Publication (Unexamined Application) No. 2000-175685). However, these modified enzymes were not practical with respect to instability in the slightly acidic range.

As described above, when enzymatically quantifying creatinine or creatine, the reliability of the measurements are reduced if substances such as bilirubin affect them, since the amounts of the two substances in serum or blood are extremely small. It is also known that when measurements are performed in the slightly acidic range where the effects of bilirubin etc. are small, decrease in stability occurs. To solve these problems with improvements other than of enzymatic nature, the amount of sarcosine oxidase in the active formulation had to be increased than it is normally used; buffers had to be selected appropriately; or additives had to be added. However, improvements by such means could increase the cost of measurement reagents and therefore were not practical.

The object of the present invention is to provide sarcosine oxidases which have optimal pH and show high activity in the slightly acidic range, which also have improved stability.

SUMMARY OF THE INVENTION

Consequently, the inventors investigated further into the problem mentioned above, and as a result of genetically modifying sarcosine oxidase genes from *Bacillus* genus (shown in SEQ ID NO: 2 of JP Patent Publication (Unexamined Application) No. 5-115281) (SEQ ID NO: 2), succeeded in obtaining sarcosine oxidases with improved activity in the slightly acidic range and improved stability, thus completing the present invention.

The present invention provides the following:

(1) A modified sarcosine oxidase with improved stability in the acidic range compared to wild-type sarcosine oxidases.

(2) The modified sarcosine oxidase according to item (1) having a residual activity of 90% or more after 5 hours of heat treatment at pH 6.0, 25° C., and 70% or more after 17 hours of heat treatment at pH 6.0, 25° C.

(3) The modified sarcosine oxidase according to item (2) wherein an activity against sarcosine in the acidic range is improved compared to a wild-type sarcosine oxidase.

(4) The modified sarcosine oxidase according to item (3) with a Km value of less than 6 mM against sarcosine at pH 6.5.

(5) A modified sarcosine oxidase having the following physicochemical properties:
   (a) action: hydrolyze 1 mol of sarcosine to produce 1 mol of glycine and 1 mol of formaldehyde.
   (b) optimal pH: around 6.5
   (c) stable pH range: between 6.0 and 11.0
   (d) optimal temperature: 60° C.
   (e) thermostability: around 50° C. (pH 7.5)
   (f) stability at pH 6.0: residual activity of 90% or more at 25° C., pH 6.0, 5 hours; 70% or more at 25° C., 17 hours
   (g) molecular weight: approximately 43,000 (SDS-PAGE)
   (h) Km value: 5.9 mM against sarcosine (pH 6.5)

(6) A modified sarcosine oxidase of the following (a), (b), or (c):
   (a) protein composed of the amino acid sequence represented by SEQ ID NO: 1;
   (b) protein composed of an amino acid sequence wherein one or some amino acid(s) are deleted, substituted, or added from the amino acid sequence represented by SEQ ID NO: 1, and which has sarcosine oxidase activity;
   (c) protein composed of an amino acid sequence which shows 80% or more homology to the amino acid sequence represented by SEQ ID NO: 1, and which has sarcosine oxidase activity.

(7) A sarcosine oxidase gene encoding a modified sarcosine oxidase of the following (a), (b), or (c):
   (a) protein composed of the amino acid sequence represented by SEQ ID NO: 1;
   (b) proteins composed of an amino acid sequence wherein one or some amino acid(s) are deleted, substituted, or added from the amino acid sequence represented by SEQ ID NO: 1, and which has sarcosine oxidase activity;
   (c) proteins composed of an amino acid sequence which shows 80% or more homology to the amino acid sequence represented by SEQ ID NO: 1, and which has sarcosine oxidase activity.

(8) A recombinant DNA characterized in that the sarcosine oxidase gene according to item (7) is inserted into vector DNA.

(9) A transformant or transductant comprising the recombinant DNA according to item (8).

(10) A method for preparing a modified sarcosine oxidase characterized by culturing the transformant or transductant according to item (9) in a medium, and collecting a sarcosine oxidase from the culture.

According to the present invention, sarcosine oxidases, in particular sarcosine oxidases which show optimal pH and high activity in the slightly acidic range and have improved stability can be prepared efficiently, thus making the invention is industrially useful.

Figure 1:
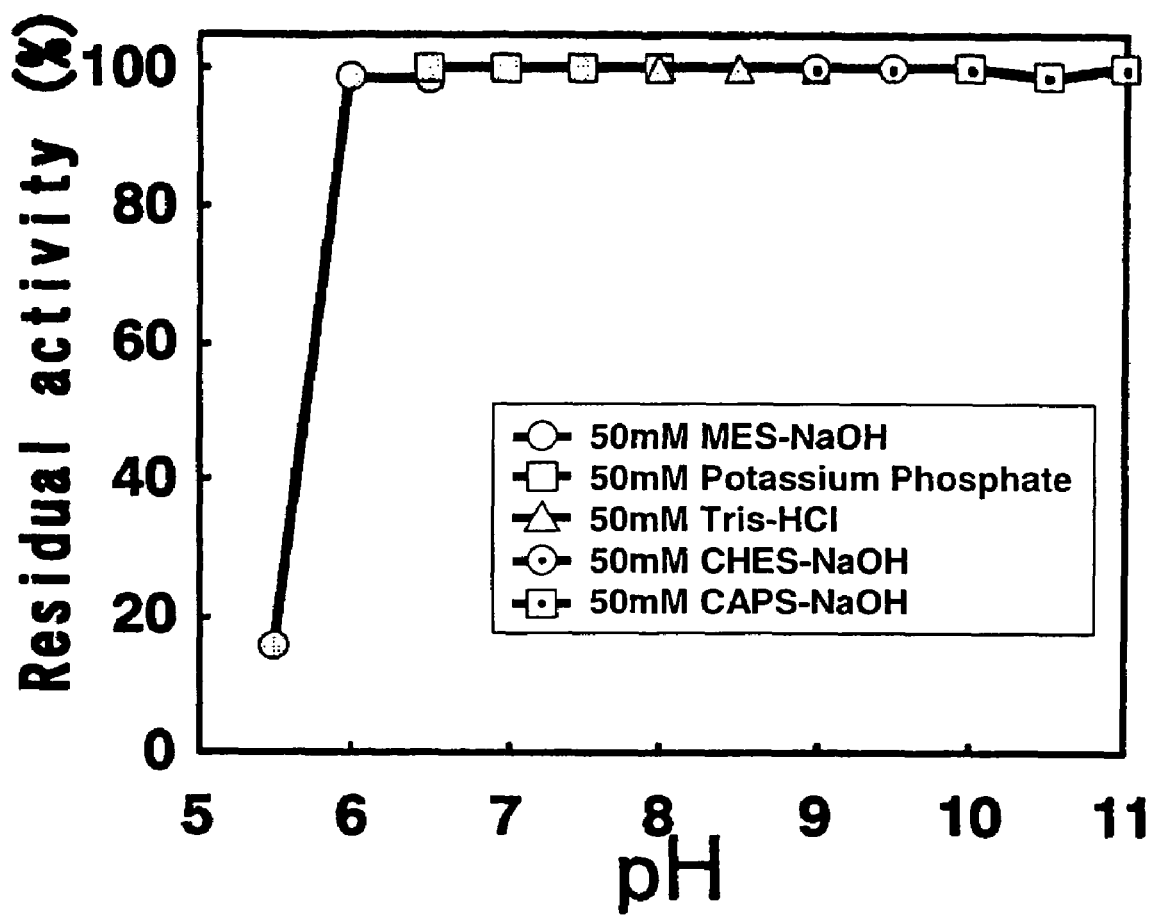
FIG. 1 shows the stable pH range of the modified sarcosine oxidase of the present invention.

This specification includes part or all of the contents as disclosed in the specifications of Japanese Patent Applications Nos. 2003-121533, 2003-396807 and 2004-116345, which are the base of the priority claim of the present application.

DETAILED DESCRIPTION OF THE PREFERRED EMBODIMENTS

The present invention will now be described in detail.

The sarcosine oxidases of the present invention can be obtained by modifying genes encoding sarcosine oxidases. Genes encoding sarcosine oxidases used for modification are not particularly limited. Specific examples of such genes include, for example, sarcosine oxidase gene from *Bacillus* genus (described in JP Patent Publication (Unexamined Application) No. 5-115281) (SEQ ID NO: 2).

Any known methods may be used as a means of modifying the above genes, and include, for example, a method of contacting a sarcosine oxidase expression plasmid vector (pSOM1) comprising sarcosine oxidase gene from *Bacillus* genus (described in JP Patent Publication (Unexamined Application) No. 5-115281) with a chemical mutagen such as hydroxylamine and nitrous acid; a method of subjecting the same to point mutation such as converting at random using PCR, or to site-directed mutagenesis which is a known technology of site-directed substitution or deletion mutation using commercially available kits; a method of selectively cleaving this recombinant plasmid DNA, then removing or adding the selected oligonucleotide, and linking the plasmid; and an oligonucleotide mutagenesis method.

Subsequently, the recombinant DNAs treated as above are purified using demineralized column such as QIAGEN (Funakoshi) to obtain various recombinant DNAs.

Using various recombinant DNAs thus obtained, *E. coli* K12, preferably *E. coli* DH5α, *E. coli* JM109 (TOYOBO), XL1-Blue (STRATAGENE) for example can be transformed or transduced to obtain transformants or transductants comprising recombinant DNAs carrying sarcosine oxidase genes with various mutations introduced.

Further, for example, in the case of transformants, the following non-limiting methods can be used to obtain strains producing sarcosine oxidases with the intended properties from the transformants obtained, which contain recombinant plasmid DNAs comprising various mutated sarcosine oxidase genes.

First, said transformants obtained are transferred to TY agar mediums with respect to each colony and cultivated. Agents such as ampicillin may be added at this time as necessary. After cultivation, colonies are transferred to two TY agar mediums as above using transfer membrane, cultivated for about 20 hours, to produce sarcosine oxidases. Inducers such as IPTG may be added at this time as necessary. After cultivation, colonies in each plate are covered with a filter, for example Hybond N+ (Amersham Pharmacia), and are attached to the filter. Then, filters on which colonies are transferred are placed on filter papers wetted with detergents for lysis treatment. After the lysis treatment, the filters are dried to prevent the colonies from running.

The two dried filters are subjected to the following process for screening. First, one of the filters is placed on a filter paper wetted with MES buffer pH 6.0 and left overnight. After drying the filter and soaking it in 500 mM Tris-HCl buffer (pH 7.7) containing sarcosine, peroxidase (or POD), Toos (or N-Ethyl-N-(2-hydroxy-3-sulfopropyl)-3-methylaniline, sodium salt, dihydrate) and 4-aminoantipyrine, intensity of purple coloring is observed. The other filter is soaked in the same solution (except using 100 mM MES buffer pH 6.5), and the intensity of the purple coloring is observed.

The results detected from the above two filters are collated, and colonies showing activity in both buffers are picked up. The colonies consequently obtained are cultivated, centrifuged to collect the bacteria, and homogenized by sonication to obtain culture supernatants. The residual activity after treatment at pH 6.0, and activity against sarcosine at pH 6.5 are measured for this sonicated culture supernatant, to obtain the desired mutant. In this way, the mutated sarcosine oxidases of the invention can be obtained.

Additionally, medium used for cultivating the above microorganisms comprises, for example, 1 or more nitrogen sources of yeast extract, peptone, meat extract, corn steep liquor, soy bean or wheat koji exudates, 1 or more inorganic salts of potassium dihydrogen phosphate, potassium hydrogen phosphate, magnesium sulfate, ferric chloride, ferric sulfate or manganese sulfate, and, further, suitable sugars and vitamins etc. as necessary.

In addition, it is appropriate to adjust the initial pH of the medium for example to 7 to 9. It is also preferred to carry out the cultivation for example at between 30 and 42° C., preferably around 37° C., for 6 to 24 hours, for example by submerged cultivation with aeration and agitation, shaking cultivation, or stationary cultivation. After cultivation, ordinary means for collecting enzymes can be used to collect modified sarcosine oxidases from the said cultures.

The cultured cells are separated from the cultures by methods including filtration and centrifugation, and washed. Modified sarcosine oxidases are preferably collected from these cells. The cells may be used as they are without further treatment, although collecting modified sarcosine oxidases from the cells using various methods for disrupting the cells such as sonic homogenizer, French press, and Dyna-Mill, methods for lysing the cell walls using cell wall degrading enzymes such as lysozyme, or methods for extracting enzymes from the cells using detergents such as Triton X-100 are preferred.

To isolate modified sarcosine oxidases from crude enzyme solution thus obtained, ordinary methods for purifying enzymes can be used. For example, it is preferred to use ammonium sulfate precipitation, precipitation with organic solvents, ion exchange chromatography, gel filtration chromatography, adsorption chromatography, electrophoresis, or suitable combinations thereof.

(Enzyme Activity)

Measurements of the activity of the enzymes according to the present invention were performed under the following condition. Enzyme activity capable of generating 1 micromol of urea per minute is defined as 1 unit.

(Preparation of Reagents)

The following solutions were prepared as reaction reagents.
1) 0.2 M sarcosine, 100 mM Tris-HCl, 2 mM KCl, 0.05% Triton-X100 pH 7.7 (activity measurement solution)
2) 80 U/ml POD solution
3) 0.2% phenol solution
4) 0.2% 4-amninoantipyrine solution
5) 0.3% SDS solution
6) 20 mM Tris-HCl, 1 mM KCl, 0.2% BSA pH 7.7 (enzyme diluent)

Next, each of the above solutions was mixed in the following amounts to prepare activity measurement solution.
1) 5 ml
2) 1 ml
3) 2 ml
4) 1 ml Measurements were carried out as follows:
1) 0.95 ml of the activity measurement solution is preincubated at 37° C. for 5 minutes.
2) 0.05 ml of enzyme solution (adjusted to between 0.04 U/ml and 0.16 U/ml with the enzyme diluent) is added and mixed.
3) reaction is carried out at 37° C. for 10 minutes.
4) after the 10-minute reaction, the 0.3% SDS solution as above is mixed in.
5) after leaving to stand at 25° C. for 10 minutes, absorbance at 495 nm is measured. (ODsample)

Blanks are measured by mixing in 0.3% SDS solution before adding the enzyme solution. (ODblank)

(Activity Conversion Formula)

$$U/ml = (OD\text{sample} - OD\text{blank}) \times 0.95$$

The present invention will now further be specifically described by means of Examples.

EXAMPLE 1

E. coli JM109 (pSOM1) containing recombinant plasmid DNA (pSOM1) (FERM BP-3604) was cultivated in LB medium (DIFCO). After collecting the bacterial cells, recombinant plasmid pSOM1 were extracted and purified from these cells using QIAGEN (QIAGEN). Approximately 100 μg of plasmid were obtained.

Using the plasmid obtained, error-prone PCR was performed with N-terminal and C-terminal primers (SEQ ID NOs: 3 and 4). In particular, Ex-taq (TAKARA SHUZO) was used with these primers under 0.075 mM manganese concentration, to carry out PCR amplification of pSOM1.

After the completion of the reaction, amplified fragments of sarcosine oxidase genes with various mutations introduced were treated with restriction enzymes Bam HI and Spe I, followed by being ligated into the vector fragment (the longer fragment) of Bam HI- and Spe I-digests of unmutated pSOM1 using T4 ligase (Boehringer).

After the ligation was complete, the reaction solution was transformed with competent Hi E. coli JM109 (TOYOBO) to prepare mutant library.

Subsequently, the mutant library was transferred to TY agar medium plates containing 50 μg/ml of ampicillin, and cultivated one day and night at 37° C. After cultivation, replicas were made on two TY agar medium plates (containing 50 μg/ml of ampicillin and 1 mM IPTG) using sterilized transfer membrane, then cultivated at 37° C. for one day and night.

Following the completion of the cultivation, the plated were cooled to 4° C. for 20 minutes, and covered with Hybond N+ (Amersham Pharmacia), and the colonies were transferred to filters. The filters on which the colonies were transferred were placed on a filter paper wetted with Bug-Buster (TAKARA SHUZO) to lyse the bacteria. The lysed filter was dried in a thermostat at 37° C.

One of the dried filters was placed on a filter paper wetted with 100 mM MES buffer pH 6.0 and left at 25° C. overnight. After this procedure, the filter was dried, and then coloring reaction was carried out using a solution of 100 mM sarcosine (TOKYO KASEI KOGYO), 500 mM Tris-HCl (WAKO PURE CHEMICAL INDUSTRIES), pH 7.7, 0.2 mM Toos (DOJINDO LABORATORIES), 0.16 mM 4-aminoantipyrine (TOKYO KASEI KOGYO), and 10 U/ml of POD (KIKKOMAN). Strains which showed more intense color on the filter compared to control strains were selected as candidate strains producing enzymes with excellent stability under acidic conditions.

The other filter was subjected to coloring reaction on a filter paper wetted with a solution of 0.12 mM sarcosine (TOKYO KASEI KOGYO), 100 mM MES (DOJINDO LABORATORIES), 0.2 mM Toos (DOJINDO LABORATORIES), 10 U/ml of POD (KIKKOMAN), and 0.16 mM 4-aminoantipyrine (TOKYO KASEI KOGYO) (pH 6.5). The strains which were the first to show an increase in color were selected as candidate strains producing enzymes with excellent activity under acidic conditions. From the above process, strains with excellent stability and excellent activity under acidic conditions were selected.

The selected strains were cultivated in 2 ml of TY medium containing 50 μg/ml of ampicillin and 1 mM IPTG. After 18 to 24 hours of cultivation, bacterial cells were collected by centrifugation, the medium was substituted with a solution of 20 mM Tris-HCl (pH 8.0), 1 mM KCl, pH 7.7, homogenized by sonication, and centrifuged (12000 r.p.m., 3 minutes). The activity of the supernatant obtained from the homogenization was measured under conditions of pH 7.7 and pH 6.5, and the mutants which showed a value at pH 6.5 close to the value at pH 7.7 were selected.

Next, using the homogenization supernatant of the strain with high activity at pH 6.5, stability in the slightly acidic range was evaluated. To 0.9 ml of a solution of 100 mM MES, pH 6.0, 0.1 ml of homogenate was added, and treated for 15 hours at 25° C. When the treatment was completed, 0.1 ml of the treated solution was diluted 10-fold with 0.9 ml of a solution of 200 mM Tris-HCl (pH 7.7), 1 mM KCl, and 0.2% BSA, and the activity was measured.

Mutated enzymes with improved activity and stability at pH 6.5 were prepared from the above process. Plasmids carrying the modified sarcosine oxidase genes of the above mutant was named pSOM3. The plasmid pSOM3 was deposited at the International Patent Organism Depository department at National Institute of Advanced Industrial Science and Technology as FERM BP-8370.

By determining the base sequence of sarcosine oxidases encoded by the present plasmids using CEQ 2000 DNA Sequencing System (Beckman Coulter), the sarcosine oxidases of the present invention were found to be substituted as follows: glutamate residue at amino acid 61 to lysine residue, aspartate residue at amino acid 241 to glycine residue, and glutamate residue at amino acid 324 to histidine residue (shown in SEQ ID NO: 1).

EXAMPLE 2

*E. coli* JM109(pSOM3) comprising the modified sarcosine oxidase genes obtained as above was cultivated with shaking in 100 ml of TY medium (1% bacto-tryptone, 0.5% bacto-yeast extract, 0.5% NaCl, pH 7.5) containing 50 µg/ml ampicillin for 16 hours, after which 10 ml was inoculated to 1 L of TY medium prepared similarly (except for containing 1 mM IPTG). After inoculation, it was cultivated at 120 r.p.m., 37° C. for approximately 20 hours.

Step 1 (Crude Enzyme Solution)

After the completion of cultivation, bacterial cells were collected by centrifugating 1 L of culture, and the cells were suspended in 50 ml of a solution of 20 mM Tris-HCl, 50 mM EDTA, pH 8.0. The cell suspension thus obtained was homogenized by sonication to obtain crude enzyme solution.

Step 2 (Ammonium Sulfate Precipitation)

Ammonium sulfate precipitation was performed by adding 20% ammonium sulfate to 50 ml of the crude enzyme solution obtained as above. Following ammonium sulfate precipitation, the precipitate was dissolved in a buffer of 50 mM KCl, 20 mM Tris-HCl and 2 mM EDTA.

Step 3 (DEAE-TOYOPEARL Ion Exchange Chromatography)

The above crude enzyme solution was adsorbed to a column packed with 300 ml of DEAE-TOYOPEARL (TOSO), washed with 600 ml of a solution of 100 mM KCl, 20 mM Tris-HCl, 2 mM EDTA, pH 8.0, then eluted with a solution of 150 mM KCl, 20 mM Tris-HCl, 2 mM EDTA, pH 8.0. When the elution was completed, the high purity fraction was collected, concentrated, and then dialyzed against 50 mM phosphate buffer pH 7.5 containing 150 mM KCl and 2 mM EDTA.

Step 4 (Sephadex G-75 Gel Filtration)

To a column packed with 200 ml of Sephadex G-75 (Pharmacia) bufferized with 50 mM phosphate buffer pH 7.5 containing 150 mM KCl and 2 mM EDTA, 15 ml of the enzyme solution from step 3 was charged to perform gel filtration. The activity of the purified enzyme obtained per OD 280 nm was approximately 25 U. The physicochemical properties of the sarcosine oxidase obtained were as follows.

EXAMPLE 3 pH Stability

After treating the present enzyme for 5 hours each at 25° C. in each of the following buffers, the residual activities were measured. The results were as shown in FIG. 1. From FIG. 1, it can be seen that the stable pH range was between pH 6.0 and 11.0.

50 mM MES-NaOH (pH 5.5, 6.0, 6.5)
50 mM calcium phosphate buffer (pH 6.5, 7.0, 7.5, 8.0)
50 mM Tris-HCl buffer (pH 8.0, 8.5, 9.0)
50 mM CHES-NaOH buffer (pH 9.0, 9.5, 10.0)
50 mM CAPS-NaOH (pH 10.0, 10.5, 11.0)

Optimal pH

Figure 2:
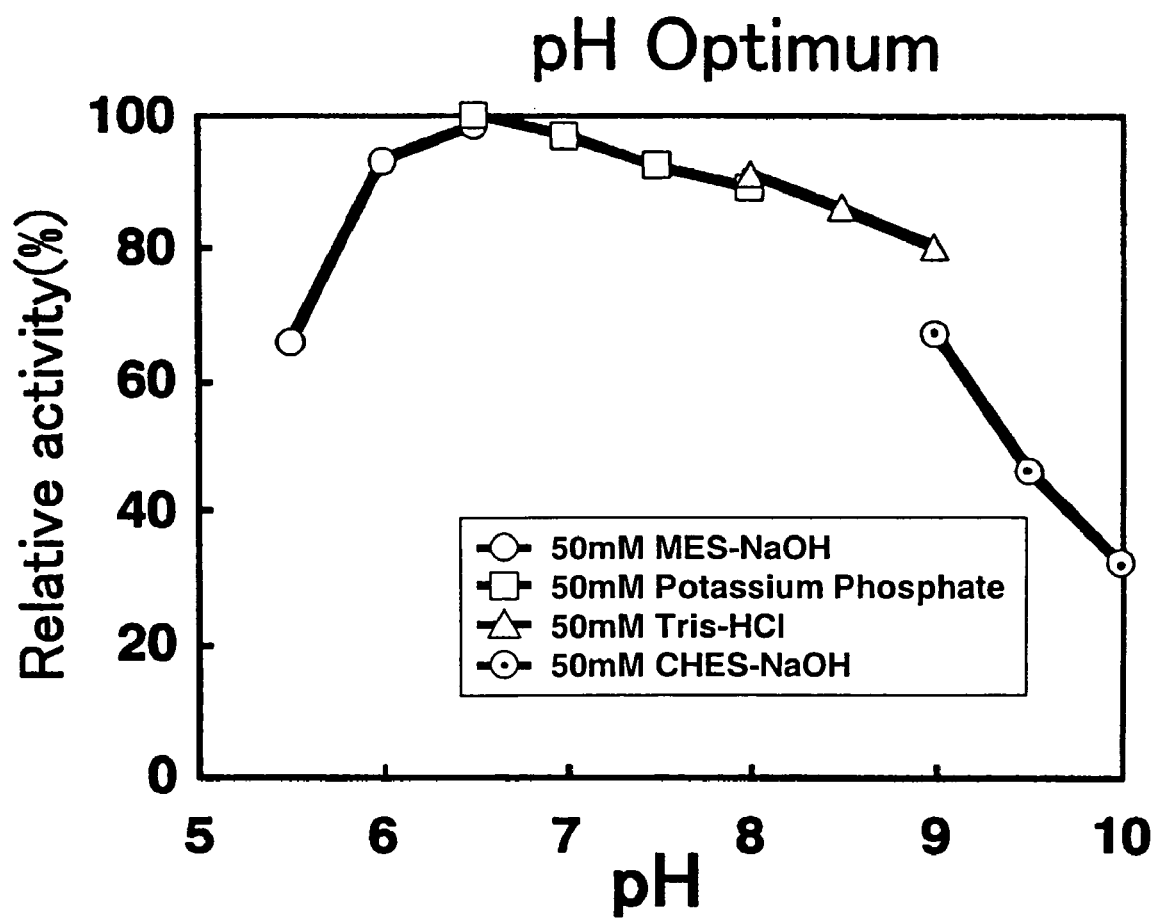
FIG. 2 shows the optimal pH of the modified sarcosine oxidase of the present invention.

When the enzyme reactions were carried out in the presence of 100 mM sarcosine, 0.2 mM Toos, 0.16 mM 4-aminoantipyrine and 10 U/ml peroxidase in each of the following buffers, the results were as shown in FIG. 2. From FIG. 2, it can be seen that the optimal pH was around 6.5.

50 mM MES-NaOH (pH 5.5, 6.0, 6.5)
50 mM potassium phosphate buffer (pH 6.5, 7.0, 7.5, 8.0)
50 mM Tris-HCl buffer (pH 8.0, 8.5, 9.0)
50 mM CHES-NaOH buffer (pH 9.0, 9.5, 10.0)

Optimal Temperature

Figure 3:
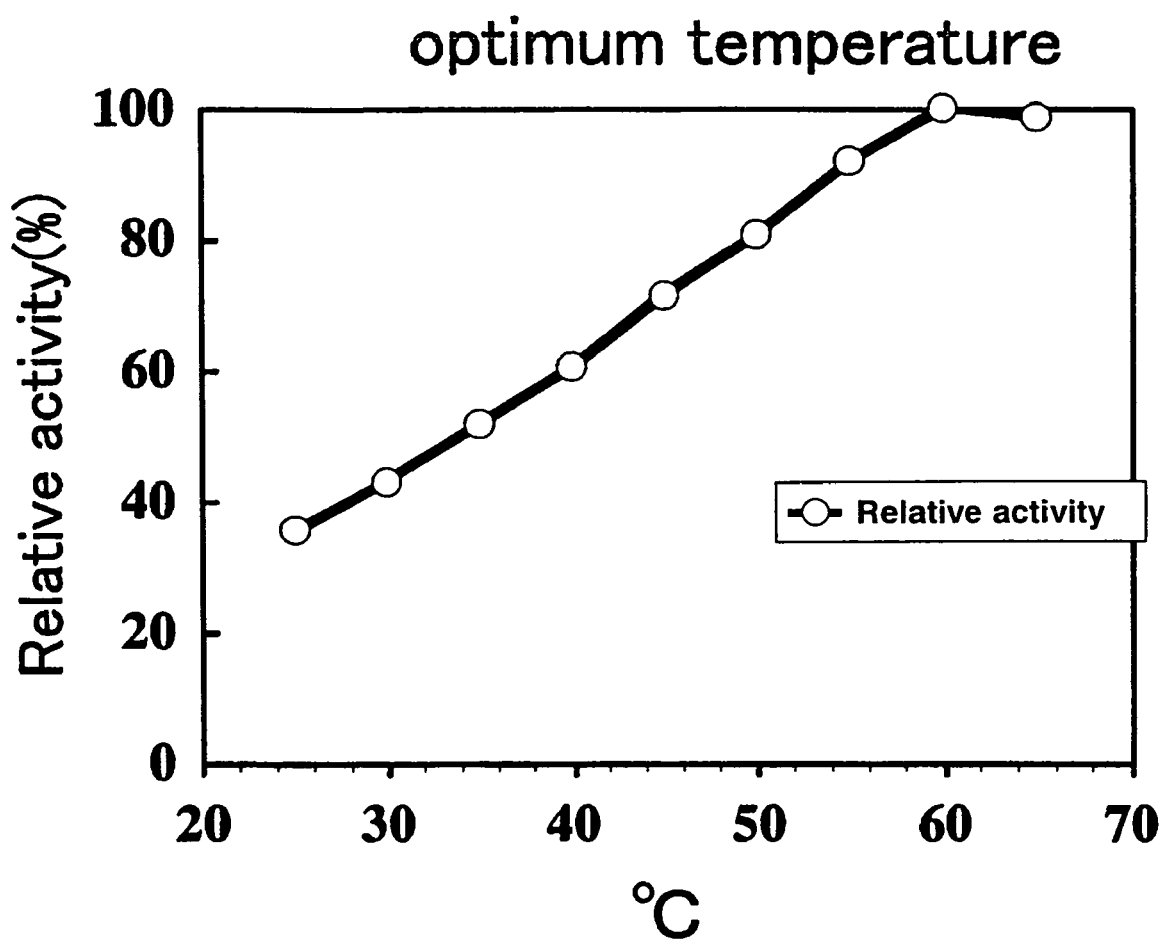
FIG. 3 shows the optimal temperature of the modified sarcosine oxidase of the present invention.

When the enzyme reactions with 100 mM sarcosine were carried out in the presence of 100 mM Tris-HCl (pH 7.7) at different temperatures, the results were as shown in FIG. 3. From FIG. 3, it can be seen that the optimal temperature was around 60° C.

Thermostability

Figure 4:
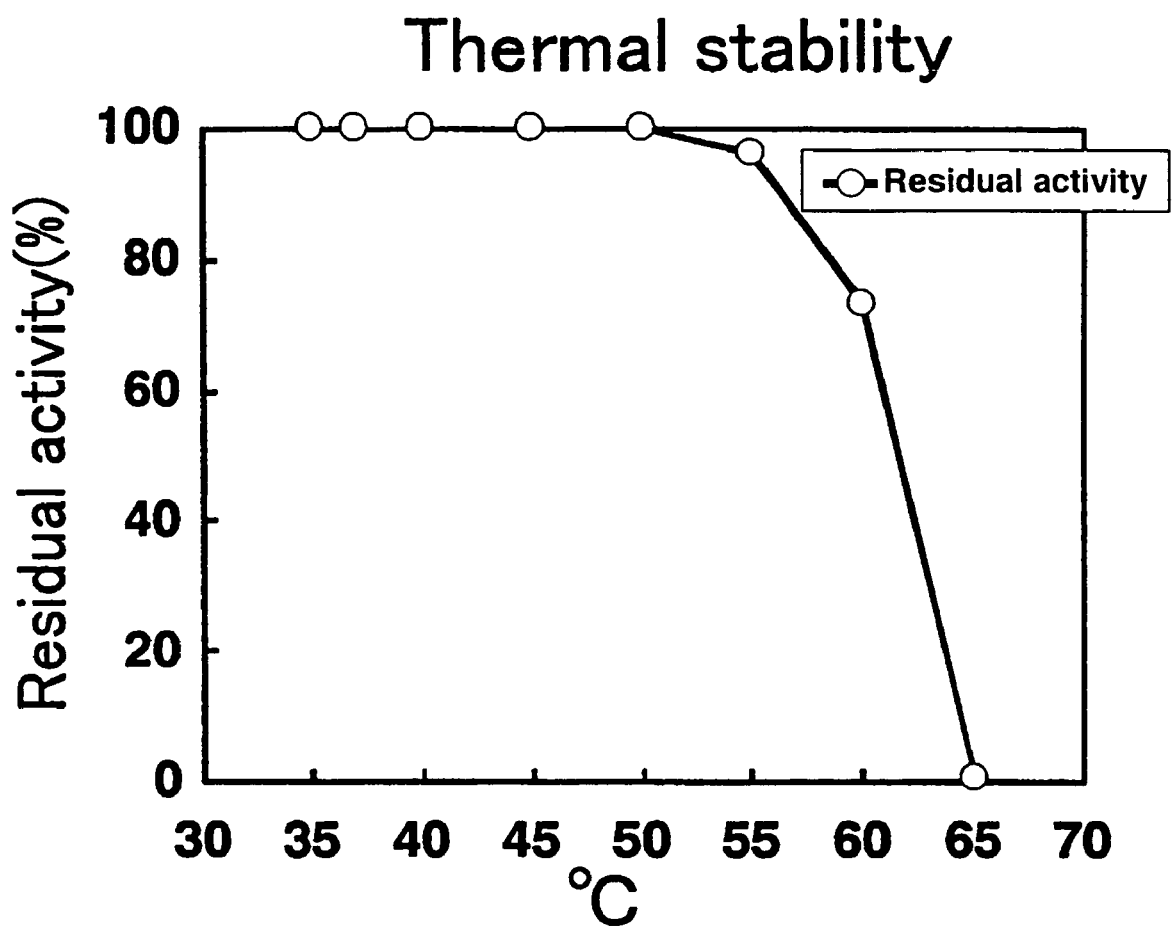
FIG. 4 shows the thermostability of the modified sarcosine oxidase of the present invention.

Heat treatments at different temperatures for 10 minutes using 50 mM potassium phosphate buffer (pH 7.5) were carried out to evaluate thermostability. The results on thermostability were as shown in FIG. 4. The present enzyme was stable up to around 50° C.

Km Value

Km values at different pH values calculated from Lineweaver-Burk calculation method were as follows. In addition, the reaction was carried out using 50 mM MES buffer (for pH 6.5 and 7.0) or Tris-HCl buffer (for pH 7.7), and using a solution of 0.2 mM Toos, 0.16 mM 4-aminoantipyrine, and 10 U/ml peroxidase as coloring agents.

As a result, the Km values at different pH were 5.9 mM (pH 6.5), 3.8 mM (pH 7.0), and 3.9 mM (pH 7.7).

EXAMPLE 4

Figure 5:
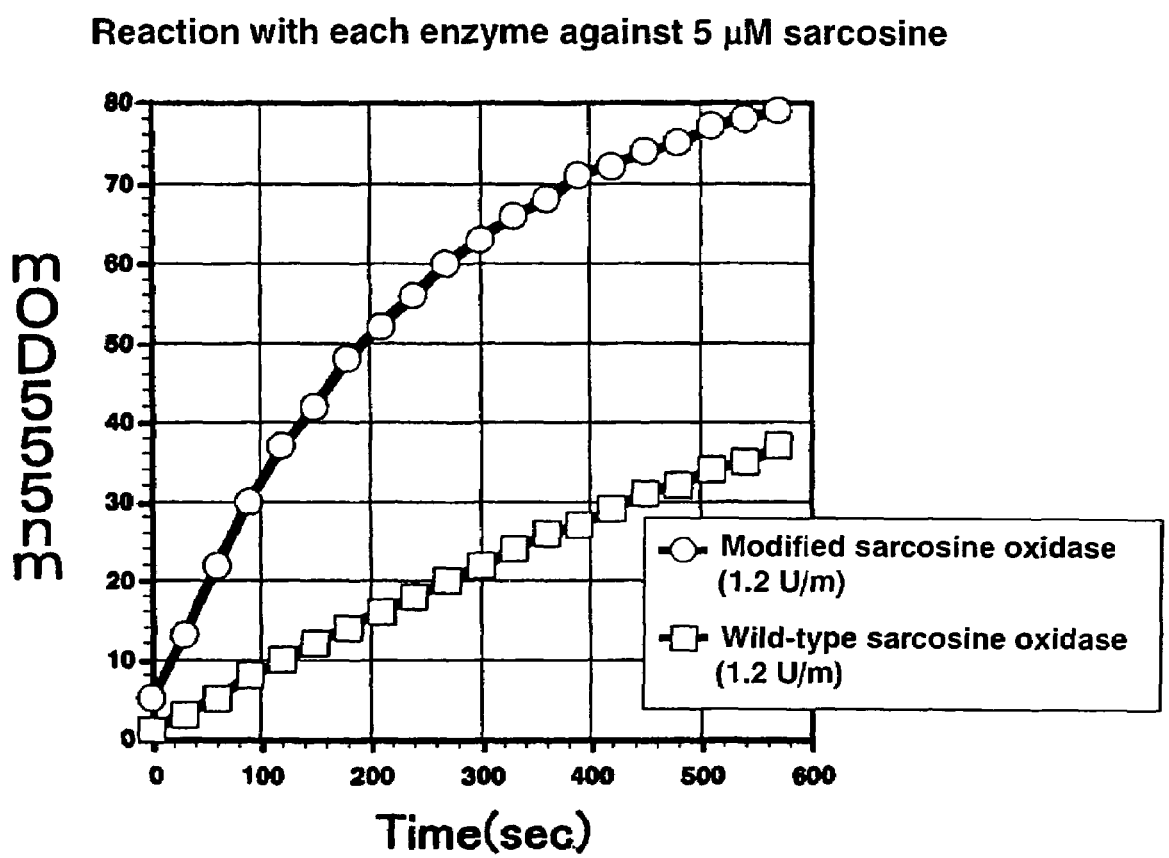
FIG. 5 shows the activity of the modified sarcosine oxidase of the present invention and of wild-type sarcosine oxidase.

Wild-type and modified sarcosine oxidase 1.2 U/ml each were subjected to reaction with 5 µM of sarcosine at 37° C., pH 6.5. The composition of the reaction solution was 50 mM MES, 60 mM NaCl, 0.2 mM Toos, 0.16 mM 4-aminoantipyrine, and 20 U/ml peroxidase. The results are shown in FIG. 5. As can be seen from FIG. 5, modified sarcosine oxidase exhibited significantly good activity at pH 6.5 compared to the wild-type.

EXAMPLE 5

Wild-type and modified sarcosine oxidase were left for 17 hours in 100 mM MES (pH 6.0) at 25° C. The residual activity after the treatment was 13.6% for the wild-type, and 72.8% for the modified enzyme.

All the publications, patents and patent applications cited herein are incorporated herein by reference in their entirely.

What is claimed is:

1. A modified sarcosine oxidase wherein said enzyme
(a) hydrolyzes 1 mol of sarcosine to produce 1 mol of glycine and 1 mol of formaldehyde;
(b) has an optimal pH of about 6.5;
(c) does not change its activity after being incubated at pH of between 6.0 and 11.0 for 5 hours at 25° C.;
(d) has an optimal temperature of 60° C.;
(e) is stable after heating for 10 minutes in 50 mM potassium phosphate buffer and at pH 7.5, at about 50° C.;
(f) retains 90% of activity after 5 hours at pH 6.0 and 25° C. and it retains 70% activity after 17 hours at pH 6.0 and 25° C.;
(g) has a molecular weight of approximately 43,000 (SDS-PAGE); and
(h) has Km value of 5.9 mM at pH 6.5; and
wherein said modified sarcosine oxidase is encoded by a DNA derived by modifying a DNA having the nucleotide sequence represented by SEQ ID NO:2.

2. A modified sarcosine oxidase of the following (a):
(a) a protein consisting of the amino acid sequence represented by SEQ ID NO: 1.